United States Patent [19]

Bormann et al.

[11] 3,991,097

[45] Nov. 9, 1976

[54] PROCESS FOR THE MANUFACTURE OF SUBSTITUTED AMINO-BENZOIC ACID DERIVATIVES

[75] Inventors: Dieter Bormann, Kelkheim, Taunus; Wulf Merkel, Neuenhain, Taunus, both of Germany

[73] Assignee: Hoechst Aktiengesellschaft, Frankfurt am Main, Germany

[22] Filed: Sept. 5, 1974

[21] Appl. No.: 503,280

[30] Foreign Application Priority Data

Sept. 7, 1973 Germany............................. 2345229

[52] U.S. Cl............................. 260/470; 260/239 N; 260/239 E; 260/293.73; 260/326.35; 260/326.36; 260/326.4; 260/327 TH; 260/332.2 R; 260/345.7; 260/345.8; 260/347.2; 260/465 D; 260/516; 260/518 R; 260/518 A; 260/519

[51] Int. Cl.².................................... C07C 143/80

[58] Field of Search ........... 260/470, 516, 471, 515, 260/518, 519, 518 R, 518 A, 465 D, 239 E, 239 A, 326.35, 326.36, 326.4, 293.73, 345.7, 345.8, 347.2, 327 TH, 332.2 R

[56] References Cited

UNITED STATES PATENTS 3,806,534    4/1974    Feit et al............................. 260/516

OTHER PUBLICATIONS

Fieser, et al., "Reagents for Organic Synthesis" Wiley & Sons, Inc. (1967) vol. I 1053–1054.
Fieser et al. "Reagents for Organic Synthesis" Wiley & Sons, Inc. (1969) vol. 2 106–107.
March "Advanced Organic Chemistry," McGraw–Hill (N.Y.) 1968, pp. 891–895.

*Primary Examiner*—Richard L. Raymond
*Attorney, Agent, or Firm*—Curtis, Morris & Safford

[57] ABSTRACT

3-Alkylamino-5-sulfamyl benzoic acid derivatives are prepared by reducing 3-acylamino-5-sulfamyl-benzoic acid derivatives by means of boron hydrides or complex boron hydrides in the presence of Lewis acids.

6 Claims, No Drawings

PROCESS FOR THE MANUFACTURE OF SUBSTITUTED AMINO-BENZOIC ACID DERIVATIVES

The present invention relates to a process for the manufacture of 3-alkylamino-5-sulfamyl-benzoic acid derivatives.

The derivatives prepared according to the process of the invention correspond to the formula I

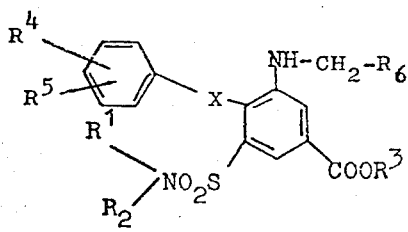

in which $R^1$ and $R^2$ may be the same or different and each stands for hydrogen or alkyl of 1 to 4 carbon atoms and, if $R^1$ stands for hydrogen, $R^2$ may also stand for alkoxymethyl of 1 to 10 carbon atoms in the alkyl moiety, phenoxymethyl or phenylthiomethyl, $R^3$ stands for hydrogen, a straight-chained or branched alkyl group of 1 to 6 carbon atoms, cycloalkyl of 5 or 6 carbon atoms in the ring, one of which may be replaced by oxygen or sulfur, $R^3$ stands furthermore for phenyl or benzyl which may be substituted in the phenyl group by nitro, alkyl of 1 to 3 carbon atoms, alkoxy of 1 to 5 carbon atoms or halogen, or benzhydryl, $R^4$ and $R^5$ may be the same or different and each stands for hydrogen, hydroxy, nitro, chlorine, alkyl or alkoxy of 1 to 5 carbon atoms, amino, mono- or dialkylamino, each having 1 to 5 carbon atoms in the alkyl moiety, and in which the nitrogen atom of the amino group may also be a member of a saturated heterocyclic 3- to 6-membered ring. $R^6$ stands for a straight-chained or branched alkyl group of 1 to 4 carbon atoms, which may include oxygen, nitrogen or sulfur atoms and may be substituted by halogen, hydroxy, mercapto, cyano or amino groups; a carbocyclic ring having 3 to 5 carbon atoms, or phenyl or benzyl groups which may carry in the phenyl radical the substituents $R^4$ or $R^5$ which are defined as above, and X stands for oxygen, sulfur or a methylene group.

The process of the present invention comprises reducing a 3-acylamino-5-sulfamyl-benzoic acid derivative of the formula II

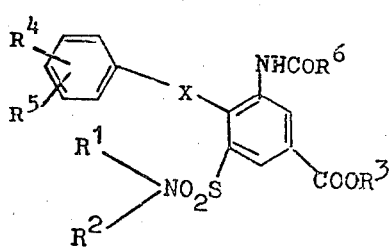

in which $R^1$ to $R^6$ and X are defined as above, by means of a boron hydride or a complex boron hydride in the presence of a Lewis acid and, where required, subjecting the 3-amino-5-sulfamyl-benzoic acid ester of formula I, in which $R^3$ is not hydrogen, to a hydrolysis, hydrogenolysis or an elimination reaction.

The products of the invention have good diuretic properties.

Some of the 3-N-alkylamino-4-phenoxy-5-sulfamyl-benzoic acid derivatives of formula I have been known for some time. The hitherto known process for the manufacture of the known compounds is, in many cases, not satisfactory. It is carried out, for example by heating the amino compound of formula III ($R^1$ to $R^3$ stand for hydrogen) in the presence of concentrated sulfuric acid and butanol under reflux. After several days, the butyl ester of the desired product has formed and has to be hydrolyzed. Owing to the long reaction times and the risk of dialkylation, attempts had to be made to prepare the compounds of the general formula I under mild conditions with better space-time yields.

The surprising feature of the process of the invention is that the acylamino group can be reduced by adding diborane or a complex boron hydride in the presence of a Lewis acid without any change of the other groups present in the molecule. The process affords good yields. When the reaction is complete, the 3-alkylamino-5-sulfamyl-benzoic acids may be, where required, set free from the carboxylic acid esters by hydrolysis, hydrogenolysis or an elimination reaction.

The 3-acylamino-5-sulfamyl-benzoic acid derivatives of formula II used for the present invention may be obtained by various methods, for example from 3-amino-5-sulfamyl-benzoic acid derivatives of the general formula III

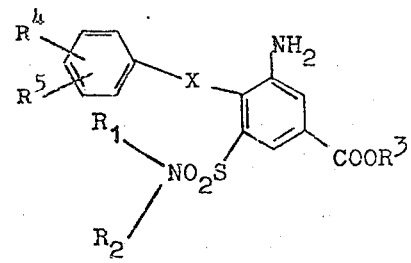

in which X and $R^1$ to $R^5$ are defined as above, by reacting in the usual manner these amino compounds with carboxylic acid derivatives capable of forming amides, for example carboxylic acid anhydride or halides.

Most of the amino compounds of formula III, required for the acylation, are known. The alkoxymethyl, phenoxymethyl and phenylthiomethylsulfamyl derivatives of the 4-phenoxy compounds are obtained, for example by reacting 3-nitro-4-phenoxy-5-sulfamyl-benzoic acid esters with formaldehyde and alcohol and subsequently reducing the nitro group.

The 3-aminobenzoic acid derivatives of formula III may be obtained as free acids or in the form of their esters and may be reacted as such.

The corresponding 3-acylamino-benzoic acid derivatives of formula II are then reduced according to the process of the invention by means of boron hydride or a complex boron hydride in the presence of a Lewis acid.

For this purpose, they may be used as free carboxylic acids. It is, however, advantageous, prior to the reduction, to convert the carboxylic acid into a salt which does not hinder the reduction, for example an alkali or alkaline earth metal salt. To obtain particularly pure reaction products with a high yield, it is especially advantageous to use 3-acylamino-5-sulfamyl-benzoic acid esters for the reduction.

The esters can be prepared according to methods known in the literature of the art. As esters, alkyl esters of 1 to 5 carbon atoms, such as methyl ester, ethyl ester of n-pentyl ester, benzyl ester which may be substituted in the phenyl group by halogen, alkoxy of 1 to 5 carbon atoms or nitro, for example benzyl ester or p-methoxybenzyl ester or tert.-butyl ester and benzhydryl ester, are especially useful.

As reducing agents, various boron hydrides, for example diborane are mentioned. They can be introduced into the reaction mixture while using special care, for example employing nitrogen as an inert gas. For a simpler handling of the reaction, the boron hydrides, for example diborane, are dissolved in a solvent and the solution is used for the reduction. As solvents, ethers, for example tetrahydrofuran or diethyleneglycol dimethyl ether, are especially useful.

Diborane which is used for the reduction may be prepared by various methods, for example by reacting boron trichloride with LiAlH$_4$ according to the equation:

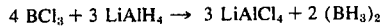
$$4\ BCl_3 + 3\ LiAlH_4 \rightarrow 3\ LiAlCl_4 + 2\ (BH_3)_2$$

or from tetraalkylammonium boranate and alkyl halides (cf. Tetrahedron Letters 1972, 3173).

Alternatively, the same reduction of the 3-acylamino compounds of formula II is effected by allowing complex boron hydrides to act on them in the presence of Lewis acids. The complex hydrides of boron used for this reduction method are, for example, alkali metal boranates, such as lithium boron hydride, sodium boron hydride or potassium boron hydride, or alkaline earth metal boranates, such as calcium boron hydride, but also zinc boron hydride or aluminum boron hydride. With an addition of Lewis acids, these boron hydrides reduce the 3-acylamino group to the 3-alkylamino group without appreciably affecting the carboxylic acid ester function.

As Lewis acids to be used according to the invention, especially aluminum chloride, titanium tetrachloride, tin tetrachloride, cobalt dichloride, iron trichloride, mercury monochloride, zinc chloride and boron trifluoride and addition products thereof, such as boron trifluoride etherate, are to be mentioned. There is the possibility of diborane being formed during the reaction of boron trifluoride etherate, for example with sodium boron hydride (cf. Fieser, Fieser: Reagents for Organic Synthesis, John Wiley and Sons, Inc., New York, Vol 1, p. 199):

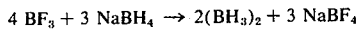
$$4\ BF_3 + 3\ NaBH_4 \rightarrow 2(BH_3)_2 + 3\ NaBF_4$$

To obtain a high throughput, the reducing agent has to be used in at least a stoichiometric amount, more advantageously in an even higher amount. The amount of the Lewis acid may be the same, but it is often sufficient to use the Lewis acid in a stoichiometric amount, calculated on the substance to be reduced, and to use the complex boron hydrides in an excess.

So, very satisfactory results are obtained, for example using for the titanium tetrachloride four times the stoichiometric amount of NaBH$_4$, whilst for boron trifluoride etherate the stoichiometric amount of sodium boron hydride is sufficient.

A list of complex compounds to be used for the reaction of NaBH$_4$ with Lewis acids is, for example given by Fieser/Fieser: Reagents for Organic Synthesis, John Wiley and Sons Inc., New York, esp. Vol I, pages 1053 to 1054; Vol II, pages 430 to 431 and; Vol III, pages 264 to 265.

For an easier handling of the reaction, it is advantageous to carry out the reduction in a solvent. As solvents, those are especially useful which have no adverse effect on the reduction, for example ethers, such as tetrahydrofuran or diethylene-glycol dimethyl ether. The solvent, in which the reduction is carried out, may be the same as that in which the boron hydride is dissolved but it may also be different.

The reduction may be carried out at a temperature which varies greatly. The temperature depends on which class of substance (acid or ester) and which reducing agent are to be used. It has proved to be especially advantageous to carry out the reduction at room temperature or at a slightly elevated temperature. If longer reaction times do not matter, the reduction may also be effected in the cold. The reaction time greatly depends on the reaction components used, on the amount to be reacted and on the temperature chosen.

According to a preferable embodiment of the process of the invention, the acylamino-sulfamyl-benzoic acid derivatives of formula II are dissolved in an inert solvent and a solution of boron hydride in the same or a different solvent is added dropwise at room temperature.

To accelerate the reaction speed, the temperature may also be raised, advantageously to 60°–80° C for about 1 hour, after the addition is complete. In another embodiment, the Lewis acid is added at room temperature to a mixture of the substance to be reduced and the complex boron hydride. A complex boron hydride, which is very readily available, is in particular sodium boron hydride which is activated by means of the aforecited Lewis acids, for example boron trifluoride etherate, aluminum chloride or titanium tetrachloride. When complex boron hydrides are used, it is especially advantageous to introduce the substance to be reduced together with the Lewis acid into the reactor and then to add the complex boron hydride dissolved dropwise.

To accelerate the reaction rate, it is advantageous to heat the mixture for about 1 to 4 hours to 50°–150° C, preferably 50° to 70° C, when the addition is complete.

When, for example an acylamino-benzoic acid ester of formula II is used for the reduction, a control thin-layer chromatogram indicates, upon heating, the formation of the desired 3-alkylamino-5-sulfamyl-benzoic acid ester.

The end products can be isolated by various methods, depending on whether the end product of the reduction is to be the free acid or the corresponding 3-alkylamino-sulfamyl-benzoic acid ester.

A preferable working-up method consists in freeing the solution of the reaction product from reducing agents, if any, by adding small amounts of an acid and precipitating the 3-alkylamino-5-sulfamyl-benzoic acid ester by subsequent addition of a non-solvent. When diethylene-glycol dimethyl ether is used, an especially favorable non-solvent is water. The 3-alkylamino-benzoic acid esters crystallize, in most cases, with a high degree of purity in an almost quantitative yield.

The esters can be converted subsequently, where desired, into the free N-alkylamino-sulfamyl-benzoic acids of formula I ($R^3$ for hydrogen) by hydrolysis, but in particular by hydrogenolysis or by an elimination reaction.

According to another method for isolating the 3-alkylamino-sulfamyl-benzoic acids of formula I ($R^3$ stands for hydrogen), part of the reaction mixture is concentrated, after excess reducing agent has been destroyed, a dilute base is added and, where required, the mixture is heated for a short time. The base used is, for example a sodium hydroxide solution. The 3-alkylamino-5-sulfamyl-benzoic acids can be isolated in the form of salts but also, if desired, in the form of the free acids of formula I ($R^3$ stands for hydrogen) by acidification.

The extremely smooth acylation reaction of the amino compounds of formula III and the subsequent reduction of the 3-acylamino-sulfamyl-benzoic acid derivatives of formula II provide the 3-alkylamino-sulfamyl-benzoic acid derivatives of formula I in a high purity and a high space-time yield. Due to an easy recovery of the solvents used for the reaction and to the small amount of by-products, this process is particularly advantageous as far as environmental protection is concerned.

According to the process of the invention, the following compounds of formula I can preferably be prepared, in addition to those already known:
Ethyl 3-butylamino-4-phenoxy-5-sulfamyl-benzoate,
n-pentyl 3-butylamino-4-phenoxy-5-sulfamyl-benzoate,
n-hexyl 3-butylamino-4-phenoxy-5-sulfamyl-benzoate,
tert-butyl 3-butylamino-4-phenoxy-5-sulfamyl-benzoate,
benzyl 3-butylamino-4-phenoxy-5-sulfamyl-benzoate,
p-methoxybenzyl 3-butylamino-4-phenoxy-5-sulfamyl-benzoate,
benzhydryl 3-butylamino-4-phenoxy-5-sulfamyl-benzoate,
tetrahydropyranyl 3-butylamino-4-phenoxy-5-sulfamyl-benzoate,
pivaloyloxymethyl 3-butylamino-4-phenoxy-5-sulfamyl-benzoate,
tert.-butyl 5-methoxymethyl-sulfamyl-3-butylamino-4-phenoxybenzoate,
benzyl 5-methoxymethyl-sulfamyl-3-butylamino-4-phenoxy-benzoate,
benzhydryl 5-methoxymethyl-sulfamyl-3-butylamino-4-phenoxybenzoate,
p-methoxybenzyl 5-methoxymethyl-sulfamyl-3-butylamino-4-phenoxy-benzoate,
p-nitrobenzyl 5-methoxymethyl-sulfamyl-3-butylamino-4-phenoxybenzoate,
tert.-butyl 5-butoxymethylsulfamyl-3-butylamino-4-phenoxy-benzoate,
benzyl 5-butoxymethylsulfamyl-3-butylamino-4-phenoxy-benzoate,
benzhydryl 5-butoxymethylsulfamyl-3-butylamino-4-phenoxy-benzoate,
p-methoxybenzyl 5-butoxymethylsulfamyl-3-butylamino-4-phenoxy-benzoate,
p-nitrobenzyl 5-butoxymethylsulfamyl-3-butylamino-4-phenoxy-benzoate,
tert-butyl 5-decyloxymethylsulfamyl-3-butylamino-4-phenoxy-benzoate,
benzyl 5-decyloxymethylsulfamyl-3-butylamino-4-phenoxy-benzoate,
benzhydryl 5-decyloxymethylsulfamyl-3-butylamino-4-phenoxy-benzoate,
p-methoxybenzyl 5-decyloxymethylsulfamyl-3-butylamino-4-phenoxy-benzoate,
p-nitrobenzyl 5-decyloxymethylsulfamyl-3-butylamino-4-phenoxy-benzoate,
benzyl 5-methylsulfamyl-3-butylamino-4-phenoxy-benzoate,
tert-butyl 5-butylsulfamyl-3-butylamino-4-phenoxy-benzoate,
methyl 5-benzylsulfamyl-3-butylamino-4-phenoxy-benzoate,
benzhydryl 5-dimethylsulfamyl-3-butylamino-4-phenoxy-benzoate and
n-hexyl 5-phenylsulfamyl-3-butylamino-4-phenoxy-benzoate.

Instead of the above-cited products of the invention, those in which the moiety "-4-phenoxy-" carries further substituents, such as to read -4'-chlorophenoxy-, -4'-methylphenoxy-, -4'-methoxyphenoxy-, -4'-aminophenoxy-, -4'-nitrophenoxy-, -4'-ethylaminophenoxy-, -2',4'-dimethylphenoxy-, -3',4'-dimethoxyphenoxy-, -2',4'-dichlorophenoxy-, -3'-trifluoromethyl-phenoxy-, as well as all the free carboxylic acids of the aforecited benzoates, may also be mentioned.

According to the process of the invention, the following compounds of the general formula I may preferably be prepared:
3-Cyclopropylmethylamino-4-phenoxy-5-sulfamyl-benzoic acid
3-cyclopropylmethylamino-4-(4'-chlorophenoxy)-5-sulfamyl-benzoic acid
3-cyclopropylmethylamino-4-(4'-methylphenoxy)-5-sulfamyl-benzoic acid
3-cyclopropylmethylamino-4-(4'-ethylaminophenoxy)-5-sulfamyl-benzoic acid
3-cyclopropylmethylamino-4-(4'-aminophenoxy)-5-sulfamyl-benzoic acid
3-cyclopropylmethylamino-4-(4'-methoxyphenoxy)-5-sulfamyl-benzoic acid
3-cyclopropylmethylamino-4-(4'-hydroxyphenoxy)-5-sulfamyl-benzoic acid
3-cyclopropylmethylamino-4-(4'-nitrophenoxy)-5-sulfamyl-benzoic acid
3-cyclopropylmethylamino-4-(2',4'-dimethylphenoxy)-5-sulfamyl-benzoic acid
3-cyclopropylmethylamino-4-(3',4'-dimethoxyphenoxy)-5-sulfamyl-benzoic acid
3-cyclopropylmethylamino-4-(3'-trifluorophenoxy)-5-sulfamyl-benzoic acid
3-cyclopropylmethylamino-4-phenylthio-5-sulfamyl-benzoic acid,
3-cyclopropylmethylamino-4-benzyl-5-sulfamyl-benzoic acid,
3-cyclobutylmethylamino-4-phenoxy-5-sulfamyl-benzoic acid,
3-cyclobutylmethylamino-4-phenylthio-5-sulfamyl-benzoic acid,
3-cyclobutylmethylamino-4-benzyl-5-sulfamyl-benzoic acid,
3-phenylethylamino-4-phenoxy-5-sulfamyl-benzoic acid,
3-phenylethylamino-4-(4'-chlorophenoxy)-sulfamyl-benzoic acid, 3-phenylethylamino-4-(4'-methylphenoxy)-sulfamyl-benzoic acid,
3-phenylethylamino-4-(4'-methoxyphenoxy)-sulfamyl-benzoic acid,
3-phenylethylamino-4-(4'-ethylaminophenoxy)-sulfamyl-benzoic acid,
3-phenylethylamino-4-(4'-aminophenoxy)-sulfamyl-benzoic acid,
3-phenylethylamino-4-(2',4'-dimethylphenoxy)-sulfamyl-benzoic acid,
3-phenylethylamino-4-phenylthio-5-sulfamyl-benzoic acid,
3-phenylethylamino-4-benzyl-5-sulfamyl-benzoic acid,
3-benzylamino-4-phenoxy-5-sulfamyl-benzoic acid,
3-benzylamino-4-phenylthio-5-sulfamyl-benzoic acid,
3-benzylamino-4-benzyl-5-sulfamyl-benzoic acid,
3-furfurylamino-4-phenoxy-5-sulfamyl-benzoic acid,
3-furfurylamino-4-phenylthio-5-sulfamyl-benzoic acid,
3-furfurylamino-4-benzyl-5-sulfamyl-benzoic acid,
3-(2-methoxyethylamino)-4-phenoxy-5-sulfamyl-benzoic acid,
3-(2-methoxyethylamino)-4-phenylthio-5-sulfamyl-benzoic acid,
3-(2-methoxyethylamino)-4-benzyl-5-sulfamyl-benzoic acid,
3-(2-methylthioethylamino)-4-phenoxy-5-sulfamyl-benzoic acid,
3-(2-methylthioethylamino)-4-phenylthio-5-sulfamyl-benzoic acid,
3-(2-methylthioethylamino)-4-benzyl-5-sulfamyl-benzoic acid,
3-(2-methylaminoethylamino)-4-phenoxy-5-sulfamyl-benzoic acid,
3-(2-methylaminoethylamino)-4-phenylthio-5-sulfamyl-benzoic acid,
3-(2-methylaminoethylamino)-4-benzyl-5-sulfamyl-benzoic acid,
3-(4-hydroxybutylamino)-4-phenoxy-5-sulfamyl-benzoic acid,
3-(4-hydroxybutylamino)-4-phenylthio-5-sulfamyl-benzoic acid,
3-(4-hydroxybutylamino)-4-benzyl-5-sulfamyl-benzoic acid,
3-(3-hydroxypropylamino)-4-phenoxy-5-sulfamyl-benzoic acid,
3-(3-hydroxypropylamino)-4-phenylthio-5-sulfamyl-benzoic acid,
3-(3-hydroxypropylamino)-4-benzyl-5-sulfamyl-benzoic acid,
methyl 3-(4-chlorobutylamino)-4-phenoxy-5-sulfamyl-benzoate,
methyl 3-(4-chlorobutylamino)-4-phenylthio-5-sulfamyl-benzoate,
methyl 3-(4-chlorobutylamino)-4-benzyl-5-sulfamyl-benzoate,
methyl 3-(3-chloropropylamino)-4-phenoxy-5-sulfamyl-benzoate,
methyl 3-(3-chloropropylamino)-4-phenylthio-5-sulfamyl-benzoate,
methyl 3-(3-chloropropylamino)-4-benzyl-5-sulfamyl-benzoate,
methyl 3-(2-chloroethylamino)-4-phenoxy-5-sulfamyl-benzoate,
methyl 3-(2-chloroethylamino)-4-phenylthio-5-sulfamyl-benzoate,
and methyl 3-(2-chloroethylamino)-4-benzyl-5-sulfamyl-benzoate.

The following Examples illustrate the invention.

EXAMPLE 1

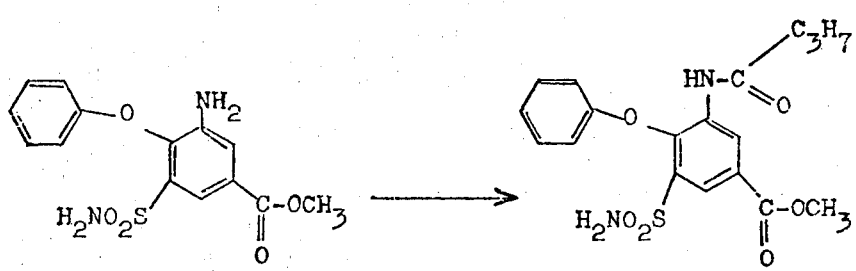

Methyl 3-n-butyrylamino-4-phenoxy-5-sulfamyl-benzoate

Method A

A solution of 9 ml of butyric acid chloride in 100 ml of acetone was slowly added dropwise while thoroughly stirring to a boiling solution of 16 g of methyl 3-amino-4-phenoxy-5-sulfamyl benzoate and 5 ml of pyridine in 100 ml of anhydrous dioxan. After about 4 hours, the reaction mixture was concentrated in a rotary evaporator. The remaining oily product was dissolved in a small amount of methanol, and this solution was added dropwise while vigorously stirring to a mixture of ice water and 2N hydrochloric acid. Methyl 3-n-butylrylamino-4-phenoxy-5-sulfamyl-benzoate precipitated with a very good yield in white flakes, m.p. 187°–194° C.

After recrystallization from methanol of ethanol, the melting point was 195°–197° C.

Method B

2 Milliliters of butyric acid chloride in 25 ml of acetone were slowly added dropwise while vigorously stirring to a boiling mixture of 3.3 g of methyl 3-amino-4-phenoxy-5-sulfamyl-benzoate and 3 g of finely powdered potassium carbonate in 100 ml of acetone. After having been refluxed for 3 hours, the product was worked up as in Method A.

Method C

An excess ether solution of diazomethane was added dropwise to a solution of 10 g of 3-n-butyrylamino-4-phenoxy-5-sulfamyl-benzoic acid in 100 ml of tetrahydrofuran. The mixture was heated at the boil for a short time and excess diazomethane was destroyed by adding some drops of glacial acetic acid. The solution was concentrated and the reamining methyl 3-n-butyrylamino-4-phenoxy-5-sulfamyl-benzoate was recrystallized from methanol or ethanol.

EXAMPLE 2

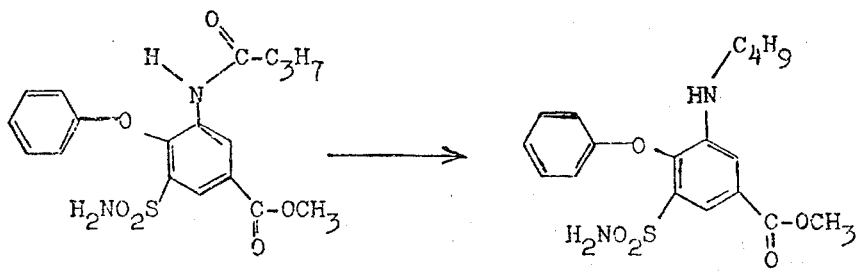

Methyl 3-n-butylamino-4-phenoxy-5-sulfamyl-benzoate

Method A

A solution of 4.55 g of boron trifluoride etherate in 50 ml of diethylene-glycol dimethyl ether (diglyme) was added dropwise while stirring to a solution of 5.9 g of methyl 3-n-butyrylamino-4-phenoxy-5-sulfamyl-benzoate and 1 g of sodium tetrahydridoborate in 200 ml of diglyme. The reaction mixture was then heated for 1 hour to 80°–90° C. After cooling, 15 ml of methanol saturated with gaseous hydrogen chloride were added, and stirring was continued for another hour. Upon the addition of water to the hot solution freed from excess hydrogen chloride, the methyl 3-n-butylamino-4-phenoxy-5-sulfamyl-benzoate, m.p. 146° C, crystallized in a practically pure form and with a very good yield (80–90 %). After recrystallization from methanol: m.p. 149°–150° C. The reaction could successfully be carried out also in tetrahydrofuran.

Method B

A solution of 1.3 g of aluminum trichloride in 50 ml of diglyme was added dropwise, slowly and with thorough stirring, to a solution of 4 g of methyl 3-n-butyrylamino-4-phenoxy-5-sulfamyl-benzoate and 1.2 g of sodium tetrahydridoborate in 100 ml of diglyme. The mixture was heated for about 1 hour to 60°–80° C and then excess reducing agent was destroyed by adding 2N acetic acid.

Method C

A solution of 1 g of titanium tetrachloride in 50 ml of diglyme was slowly added dropwise to a solution of 4 g of methyl 3-n-butyrylamino-4-phenoxy-5-sulfamyl-benzoate and 1.5 g of sodium tetrahydridoborate in 100 ml of diglyme. The solution foamed up and a blue-green precipitate formed. The mixture was heated to 60°–80° C for about 3 hours while carefully stirring, and then 2N acetic acid was added precautiously. The methyl 3-n-butylamino-4-phenoxy-5-sulfamyl-benzoate was isolated from the filtrate as in Method A.

EXAMPLE 3

3-n-butylamino-4-phenoxy-5-sulfamyl-benzoic acid 2.5 Grams of methyl 3-n-butylamino-4-phenoxy-5-sulfamyl-benzoate were dissolved in 50 ml of 1N NaOH and the solution was heated for 30 minutes on a steam bath. The solution was then filtered and carefully acidified. 3-n-butylamino-4-phenoxy-5-sulfamyl-benzoic acid precipitation in flakes which melted at 229°–231° C. After recrystallization from ethanol/water, the melting point was 235° C.

EXAMPLE 4

3-n-butyrylamino-4-phenoxy-5-sulfamyl-benzoic acid

A solution of 70 g of butyric acid chloride in 300 ml of acetone was slowly added dropwise while vigorously stirring to a boiling solution of 93 g of 3-amino-4-phenoxy-5-sulfamyl-benzoic acid and 48 g of pyridine in 500 ml of dioxan. After 7 hours, the reaction mixture was allowed to cool. It was filtered, concentrated to one third of the volume of the solvent and then added dropwise while carefully stirring to a mixture of ice water and 2N hydrochloric acid. The 3-butyrylamino-4-phenoxy-5-sulfamyl-benzoic acid which had precipitated could be recrystallized from water/methanol or from glacial acetic acid.

Melting point: 270°–271° C.

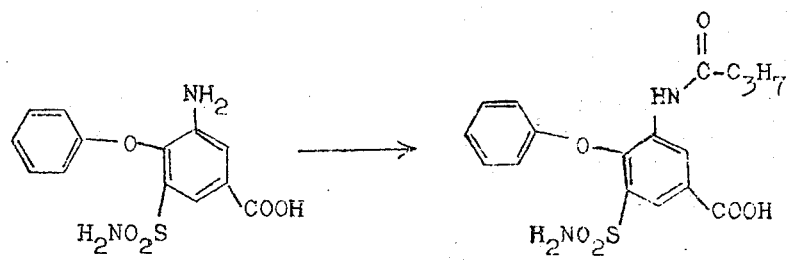

EXAMPLE 5

3-n-butylamino-4-phenoxy-5-sulfamyl-benzoic acid

A solution of 1.5 g of aluminum trichloride in diglyme was added dropwise to a mixture of 6.3 g of sodium 3-n-butyrylamino-4-phenoxy-5-sulfamyl-benzoate and 1.2 g of sodium tetrahydrido-borate in diglyme. The reaction mixture was then heated while vigorously stirring to 110°–120° C for 3 hours, and finally water was added. The reaction mixture was concentrated in a rotary evaporator. The remaining oily substance was dissolved in a small amount of a 2N ammonia solution and evaporated to dryness. Upon addition of a small amount of water, the ammonium salt of 3-n-butylamino-4-phenoxy-5-sulfamyl-benzoic acid precipitated. It was dissolved in water/methanol and a few drops of 2N hydrochloric acid were added. 3-n-butylamino-4-phenoxy-5-sulfamyl-benzoic acid crystallized.

TABLE
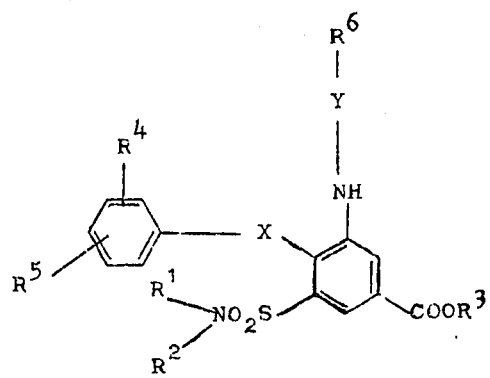
| Example No. | R¹ | R² | R³ | R⁴ | R⁵ | R⁶ |
|---|---|---|---|---|---|---|
| 6 | H | H | CH₃ | H | H | cyclopropyl |
| 7 | H | H | CH₃ | H | H | cyclopropyl |
| 8 | H | H | H | H | H | cyclopropyl |
| 9 | H | H | CH₃ | H | H | cyclobutyl |
| 10 | H | H | CH₃ | H | H | cyclobutyl |
| 11 | H | H | H | H | H | cyclobutyl |
| 12 | H | H | CH₃ | H | H | cyclopentyl |
| 13 | H | H | CH₃ | H | H | cyclopentyl |
| 14 | H | H | H | H | H | cyclopentyl |
| 15 | H | H | CH₃ | H | H | H₃C—CH—CH₃ |
| 16 | H | H | CH₃ | H | H | H₃C—CH—CH₃ |
| 17 | H | H | H | H | H | H₃C—CH—CH₃ |

| | | | | | | |
|---|---|---|---|---|---|---|
| 18 | H | H | CH₃ | H | H | H₃C—C(CH₃)₂—CH₃ |
| 19 | H | H | CH₃ | H | H | H₃C—C(CH₃)₂—CH₃ |
| 20 | H | H | H | H | H | H₃C—C(CH₃)₂—CH₃ |
| 21 | H | H | CH₃ | H | H | C₆H₅— |
| 22 | H | H | CH₃ | H | H | C₆H₅— |
| 23 | H | H | H | H | H | C₆H₅— |
| 24 | H | H | CH₃ | H | H | C₆H₅—CH₂— |
| 25 | H | H | CH₃ | H | H | C₆H₅—CH₂— |
| 26 | H | H | H | H | H | C₆H₅—CH₂— |
| 27 | H | H | CH₃ | H | H | CH₃—O—CH₂— |
| 28 | H | H | CH₃ | H | H | CH₃—O—CH₂— |
| 29 | H | H | H | H | H | CH₃—O—CH₂— |
| 30 | H | H | CH₃ | H | H | CH₃—O—C(=O)—CH₂—CH₂— |
| 31 | H | H | CH₃ | H | H | HO—CH(—)—CH₂—CH₂— (OH on H₂C) |
| 32 | H | H | H | H | H | HO—CH₂—CH₂—CH₂— |
| 33 | H | H | CH₃ | H | H | Cl—CH₂— |
| 34 | H | H | CH₃ | H | H | Cl—CH₂— |
| 35 | H | H | CH₃ | H | H | Cl—CH₂—CH₂— |
| 36 | H | H | CH₃ | H | H | Cl—CH₂—CH₂— |
| 37 | H | H | CH₃ | H | H | Cl—CH₂—CH₂—CH₂— |
| 38 | H | H | CH₃ | H | H | Cl—CH₂—CH₂—CH₂— |
| 39 | H | CH₃ | CH₃ | H | H | C₆H₅—O—CH₂— |

3,991,097

-continued

| | | | | | | |
|---|---|---|---|---|---|---|
| 40 | H | CH₃ | CH₃ | H | H | 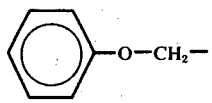 |
| 41 | H | CH₃ | H | H | H | 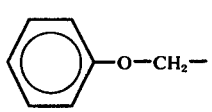 |

| Example No. | X | Y | Recrystallization from | (m.p.) | empirical formula | (molecular weight) |
|---|---|---|---|---|---|---|
| 6 | O | C=O | CH₃OH/H₂O | (212° C) | $C_{18}H_{18}N_2O_6S$ | (390,41) |
| 7 | O | CH₂ | CH₃OH | (178° C) | $C_{18}H_{20}N_2O_5S$ | (376,43) |
| 8 | O | CH₂ | glacial acetic acid | (234° C) | $C_{17}H_{18}N_2O_5S$ | (362,40) |
| 9 | O | C=O | CH₃OH | (208° C) | $C_{19}H_{20}N_2O_6S$ | (404,44) |
| 10 | O | CH₂ | CH₃OH | (169° C) | $C_{19}H_{22}N_2O_5S$ | (390,46) |
| 11 | O | CH₂ | CH₃OH/H₂O | (250° C) | $C_{18}H_{20}N_2O_5S$ | (376,43) |
| 12 | O | C=O | CH₃OH | (173° C) | $C_{20}H_{22}N_2O_6S$ | (418,47) |
| 13 | O | CH₂ | CH₃OH | (177° C) | $C_{20}H_{24}N_2O_5S$ | (404,48) |
| 14 | O | CH₂ | CH₃OH/H₂O | (156° C) | $C_{19}H_{22}N_2O_5S$ | (390,46) |
| 15 | O | C=O | CH₃OH/H₂O | (186° C) | $C_{18}H_{20}N_2O_6S$ | (392,43) |
| 16 | O | CH₂ | CH₃OH | (165° C) | $C_{18}H_{22}N_2O_5S$ | (378,4) |
| 17 | O | CH₂ | glacial acetic acid | (234° C) | $C_{17}H_{20}N_2O_5S$ | (364,42) |
| 18 | O | C=O | CH₃OH/acetone | (266° C) | $C_{19}H_{22}N_2O_6S$ | (406,46) |
| 19 | O | CH₂ | acetone/H₂O | (178° C) | $C_{19}H_{24}N_2O_5S$ | (392,47) |
| 20 | O | CH₂ | glacial acetic acid | (259° C) | $C_{18}H_{22}N_2O_5S$ | (378,45) |
| 21 | O | C=O | ethanol | (222° C) | $C_{21}H_{18}N_2O_6S$ | (426,44) |
| 22 | O | CH₂ | CH₃OH/H₂O | (179° C) | $C_{21}H_{20}N_2O_5S$ | (412,46) |
| 23 | O | CH₂ | glacial acetic acid | (251° C) | $C_{20}H_{18}N_2O_5S$ | (398,43) |
| 24 | O | C=O | CH₃OH/H₂O | (178° C) | $C_{22}H_{20}N_2O_6S$ | (440,48) |
| 25 | O | CH₂ | CH₃OH | (181° C) | $C_{22}H_{22}N_2O_5S$ | (426,50) |
| 26 | O | CH₂ | glacial acetic acid | (241° C) | $C_{21}H_{20}N_2O_5S$ | (412,46) |
| 27 | O | C=O | CH₃OH | (184° C) | $C_{17}H_{18}N_2O_7S$ | (394,40) |
| 28 | O | CH₂ | CH₃OH | (152° C) | $C_{17}H_{20}N_2O_6S$ | (380,42) |
| 29 | O | CH₂ | glacial acetic acid | (224° C) | $C_{16}H_{18}N_2O_6S$ | (366,39) |
| 30 | O | C=O | CH₃OH/H₂O | (125° C) | $C_{19}H_{20}N_2O_8S$ | (436,44) |
| 31 | O | CH₂ | n-butanol | (142° C) | $C_{18}H_{22}N_2O_6S$ | (394,45) |
| 32 | O | CH₂ | glacial acetic acid | (207° C) | $C_{17}H_{20}N_2O_6S$ | (380,42) |
| 33 | O | C=O | CH₃OH | (178° C) | $C_{16}H_{15}ClN_2O_6S$ | (398,82) |
| 34 | O | CH₂ | CH₃OH/H₂O | (175° C) | $C_{16}H_{17}ClN_2O_5S$ | (387,80) |
| 35 | O | C=O | CH₃OH/H₂O | (174° C) | $C_{17}H_{17}ClN_2O_6S$ | (412,85) |
| 36 | O | CH₂ | CH₃OH/H₂O | (117° C) | $C_{17}H_{19}ClN_2O_5S$ | (399,66) |
| 37 | O | C=O | CH₃OH | (154° C) | $C_{18}H_{19}ClN_2O_6S$ | (426,87) |
| 38 | O | CH₂ | CH₃OH | (125° C) | $C_{18}H_{21}ClN_2O_5S$ | (413,39) |
| 39 | O | C=O | acetone | (219° C) | $C_{23}H_{22}N_2O_7S$ | (470,51) |
| 40 | O | CH₂ | CH₃OH/H₂O | (171° C) | $C_{23}H_{24}N_2O_6S$ | (456,52) |
| 41 | O | CH₂ | acetone/DMF/H₂O | (271° C) | $C_{22}H_{22}N_2O_6S$ | (442,37) |

Acylation using carboxylic acid chlorides

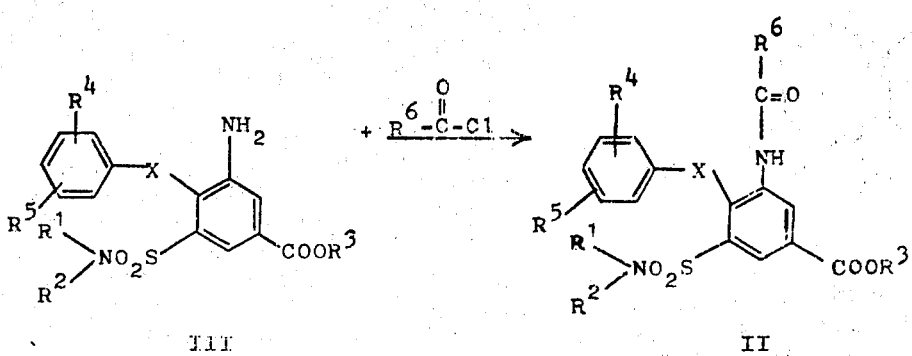

A solution of 0.1 mol of carboxylic acid chloride in 100 ml of anhydrous acetone was slowly added dropwise while thoroughly stirring to a boiling solution of 0.05 mol of the amino compound of formula III and 5 ml of pyridine in 100 ml of anhydrous dioxan. After about 2 to 5 hours, depending on the acid chloride used, the reaction was complete. The mixture was concentrated in a rotary evaporator. The remaining oily product was dissolved in a small amount of methanol or acetone, and this solution was added dropwise while vigorously stirring to ice water. The product of formula II precipitated in flakes and was suction-filtered.

Preparation of 3-alkylamino-benzoic acid derivatives of formula I

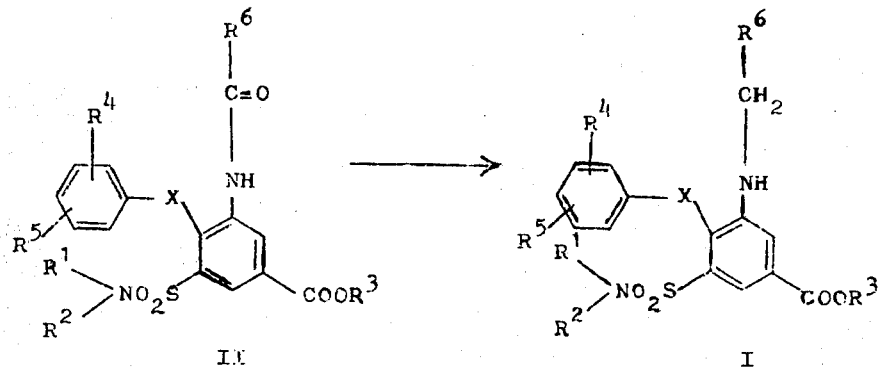

8.5 ml of $BF_3$ etherate were added to a solution or suspension of 0.03 mol of a compound of formula II in 100 to 150 ml of anhydrous diethylene-glycol dimethyl ether (diglyme). A solution of 2 g of $NaBH_4$ in 100 ml of diglyme was slowly added dropwise while thoroughly stirring at room temperature. After this addition, stirring was continued for 30 to 60 minutes at a temperature of 20° to 70° C, depending on the compound used. The end of the reaction was determined by means of thin-layer chromatography. The compounds of formula I appeared as light blue fluorescing spots on the chromatogram at 366 nm, whilst the compounds of formula II did not fluoresce.

The addition of a small amount of water (foaming!) destroyed the excess reducing agent. The mixture was filtered and the product was precipitated in the cold by adding another 200 ml of water. The product was obtained in almost pure state and was suction-filtered.

The esters thus obtained ($R^3$ not being hydrogen) could be hydrolyzed to the free acid, using 1N NaOH.

The corresponding ester was suspended in 1N NaOH and the mixture was heated on a steam bath. As soon as a clear solution was obtained, this was allowed to cool slowly and the acid was precipitated by means of 2N HCl.

The compounds obtained according to Examples 6 to 41 were prepared in accordance with the above-cited general method. Any one of the products of the invention can be prepared according to both variants given.

We claim:
1. A process for making a 3-amino-5-sulfamyl-benzoic acid ester of the formula

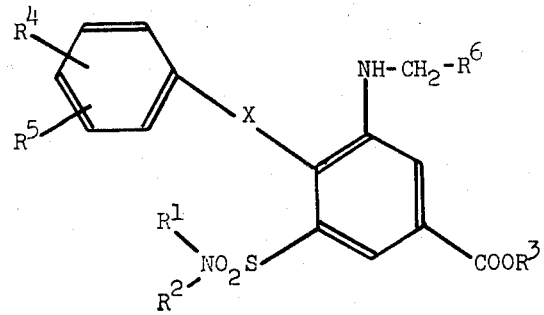

which comprises reducing a compound of the formula

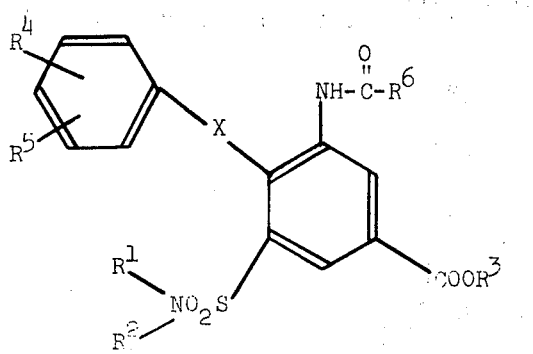

in a solvent inert to the reduction at a temperature from room temperature to 80° C., with a complex boron hydride selected from the group consisting of alkali metal boranates, alkaline earth metal boranates, zinc boron hydride, and aluminum boron hydride in the presence of a Lewis acid selected from the group consisting of aluminum chloride, titanium tetrachloride, tin tetrachloride, cobalt dichloride, iron trichloride, mercury monochloride, zinc chloride, boron trifluoride, and boron trifluoride etherate, where, in said formulas, X is oxygen, sulfur, or methylene;

$R^1$ and $R^2$, which may be the same or different, are hydrogen or alkyl having 1 to 4 carbon atoms and, if $R^1$ is hydrogen, then $R^2$ may also be alkoxymethyl having 1 to 10 carbon atoms in the alkyl moiety, phenoxymethyl, or phenylthiomethyl;

$R^3$ is a straight-chain or branched alkyl having 1 to 6 carbon atoms, cycloalkyl having 5 to 6 ring members one of which may be replaced by oxygen or sulfur, or is phenyl, benzyl, benzhydryl, or phenyl or benzyl substituted in the phenyl group by nitro, alkyl having 1 to 3 carbon atoms, alkoxy having 1 to 5 carbon atoms, or halogen;

$R^4$ and $R^5$, which are the same or different, are each hydrogen, hydroxy, nitro, chloro, alkyl or alkoxy having 1 to 5 carbon atoms, amino, monoalkylamino or dialkylamino having 1 to 5 carbon atoms in the alkyl moiety, and 3- to 6-membered saturated heterocyclic monoamino;

$R^6$ is straight-chain or branched alkyl having 1 to 4 carbon atoms which may include oxygen, sulfur, or nitrogen atoms and may be substituted by halogen, hydroxy, mercapto, cyano, or amino, or is a 3- to 5-membered carbocyclic ring, phenyl, benzyl, or phenyl or benzyl substituted in the phenyl group by hydroxy, nitro, chloro, alkyl or alkoxy having 1 to 5 carbon atoms, amino, monoalkylamino or dialkylamino having 1 to 5 carbon atoms in the alkyl moiety, and 3- to 6-membered saturated heterocyclic monoamino.

2. A process as claimed in claim 1, wherein a combination of sodium boron hydride/$BF_3$ etherate is used for the reduction.

3. A process as claimed in claim 1, wherein a combination of $NaBH_4/AlCl_3$ is used for the reduction.

4. A process as claimed in claim 1, wherein a combination of $NaBH_4/TiCl_4$ is used for the reduction.

5. A process as claimed in claim 1, wherein the reduction is carried out in diethylene-glycol dimethyl ether.

6. A process as in claim 1 wherein said 3-amino-5-sulfamyl-benzoic acid ester is subsequently converted to the corresponding benzoic acid by hydrolysis, hydrogenolysis, or an elimination reaction.

* * * * *